United States Patent
Dikovskiy et al.

(10) Patent No.: US 8,980,303 B2
(45) Date of Patent: Mar. 17, 2015

(54) ANTIMYCOTIC AND PREBIOTIC PHARMACEUTICAL COMPOSITION AND A METHOD FOR TREATING CANDIDAL VAGINITIS

(75) Inventors: Aleksander Vladimirovich Dikovskiy, Moscow (RU); Oleg Valentinovich Dorozhko, Moscow (RU); Anatolievich Bor Rudoi, Moscow (RU)

(73) Assignee: Lugs International Ltd., Road Town, Tortola (VG)

( * ) Notice: Subject to any disclaimer, the term of this patent is extended or adjusted under 35 U.S.C. 154(b) by 337 days.

(21) Appl. No.: 12/998,229

(22) PCT Filed: Sep. 30, 2008

(86) PCT No.: PCT/RU2008/000621
§ 371 (c)(1),
(2), (4) Date: Apr. 29, 2011

(87) PCT Pub. No.: WO2010/039054
PCT Pub. Date: Apr. 8, 2010

(65) Prior Publication Data
US 2011/0202025 A1 Aug. 18, 2011

(51) Int. Cl.
*A61F 6/06* (2006.01)
*A61K 31/7016* (2006.01)
(Continued)

(52) U.S. Cl.
CPC ............ *A61K 31/7016* (2013.01); *A61K 9/0034* (2013.01); *A61K 31/4174* (2013.01); *A61K 31/4196* (2013.01); *A61K 31/702* (2013.01); *A61K 45/06* (2013.01)
USPC ............... 424/430; 424/431; 514/31; 514/53; 604/360

(58) Field of Classification Search
CPC .......... A61K 31/4174; A61K 31/4196; A61K 31/7016; A61K 31/702; A61K 45/06; A61K 9/0034
USPC ........ 604/367, 360; 514/31, 53; 424/430, 431
See application file for complete search history.

(56) References Cited

U.S. PATENT DOCUMENTS 3,860,707 A * 1/1975 Wootton ......................... 514/53
4,983,393 A * 1/1991 Cohen et al. ................. 424/430
(Continued)

FOREIGN PATENT DOCUMENTS

DE 10 2004 037 505 A1 2/2006 ............... A61K 8/30
RU 2007 105 476 9/2008 ............. A61K 47/00

OTHER PUBLICATIONS

Consilium Medicum Tom 09/N 1/007, pp. 1-9, H.H. Krumko.
Supplementary European Search Report; Database EPODOC, European Patent Office, The Hague, NL, May 10, 2009, Database Accession No. RU2354385.

*Primary Examiner* — Tan-Uyen (Jackie) T Ho
*Assistant Examiner* — Peter S Vasat
(74) *Attorney, Agent, or Firm* — Nadya Reingand

(57) ABSTRACT

The invention relates to medicine and pharmacology, more particularly to a pharmaceutical composition in the form of vaginal suppositories for treating candidal vaginitis and vulvovaginitis, containing antimycotics and prebiotics. The contents of the composition for therapeutic use make it possible to achieve the synergistic effect of stimulating the growth of the normal vaginal microflora through the presence of prebiotics and inhibiting the growth and eliminating pathogenic *Candida* fungi through the presence of modern antimycotics. Furthermore, the composition substantially contains such antimycotics to which representatives of the normal flora, i.e. lactobacilli and bifidobacteria, are insensitive. The method for treating mycetogenous or bacterial vaginosis, vaginitis and vulvovaginitis is carried out with the aid of the antimycotic and prebiotic pharmaceutical composition in a medicinal form for local application.

8 Claims, 7 Drawing Sheets

(51) Int. Cl.
*A61K 9/00* (2006.01)
*A61K 31/4174* (2006.01)
*A61K 31/4196* (2006.01)
*A61K 31/702* (2006.01)
*A61K 45/06* (2006.01)

(56) References Cited

U.S. PATENT DOCUMENTS 6,455,068 B1 9/2002 Licari .......................... 424/464
2004/0110721 A1 6/2004 Zeng ............................. 514/53

* cited by examiner

ANTIMYCOTIC AND PREBIOTIC PHARMACEUTICAL COMPOSITION AND A METHOD FOR TREATING CANDIDAL VAGINITIS

CLAIM FOR PRIORITY

This non-provisional application is a national phase entry of International Application No. PCT/RU2008/000621, filed on Sep. 30, 2008, entitled "Antimycotic and Prebiotic Pharmaceutical Composition and a Method for Treating Candidal Vaginitis". The priority of International Application No. PCT/RU2008/000621 is hereby claimed and its disclosure incorporated herein by reference in its entirety.

FIELD OF INVENTION

The invention relates to medicine and pharmacology, more particularly to a new pharmaceutical antimycotic and prebiotic composition to increase considerably efficiency of candidal vaginitis and vulvovaginitis local therapy.

BACKGROUND OF THE INVENTION

Candidal vulvovaginitis is a common condition for productive-age women and one of the most frequent reasons for women to seek a medical advice. During last 10 years the number of women affected by candidal vulvovaginitis almost doubled and it is 30-45% among the infection diseases of vulva and vagina.

Candidal vaginitis is caused by yeastlike fungi *Candida*. At present more than 170 species of yeastlike fungi is described. *C. albicans* is the most frequent causative agent of a candidal vaginitis in 85-90% of women. *C. glabrata* (5-10%), *C. tropicalis* (3-5%), *C. parapsilosis* (3-5%) and *C. krusei* (1-3%) are also clinically significant among other species of *Candida*.

Significant increasing of candidal vulvovaginitis is caused by a number of predisposing factors, such as long and uncontrolled using of antibiotics, corticosteroids, cytostatics, oral contraceptives, radiation therapy, serious infectious disease, endocrine disorder, immunodeficiency state, etc. At prescription of broad spectrum antibiotics leaves out of account that they suppress not only pathogenic bacteria, but also mucous vaginas saprophytes: lactobacilli and bifidobacteria. As a result vaginal pH raises (towards to alkaline range), and disturbance of self-cleaning processes occurs. Besides, *Candida* is able to use some antibiotics as nutrient substrates. Thus favorable conditions for active overgrowth of *Candida* arises in female genital organs.

Changing the pH value of vaginal secretion is also caused by hormonal drug products. Significant growth of the number of candidal vaginitis cases mainly attributes to administration of oral contraceptives. It is reviled that administration of hormonal drug products led to growth of the glycogen concentration in vaginal epithelium cells, the epithelium becomes loosened, pH value moves to alkaline range and the nonspecific resistance decreases. In 20% of woman who administrate the oral contraceptive the tolerance to glucose is changed promoting the candidal infection changes.

Pregnancy also promotes the development of candidosis due to hormonal changes. Slump (by 60%) in rate of positive results of the fungi isolation during postnatal period indicates the connection of candidal vulvovaginitis with pregnancy.

Wearing of tight synthetic underclothes creating the microclimate with increased temperature and humidity promotes development of candidosis vulvovaginitis.

*Candida* can be isolated from a vagina of the almost healthy women in the absence of clinical signs of candidosis vulvovaginitis (carrier). These fungi become pathogenic on certain conditions under the influence of exogenous and/or endogenous factors. In the presence of essential risk factors, for example during pregnancy, any detection of *Candida* fungi in a vagina indicates candidal vulvovaginitis but not a carriage. It is confirmed by results of the following research: only 2% of pregnant women with *C. albicans* vaginal seeding displayed absence of any pathological changes.

There is the data that gastrointestinal tract is a permanent fungi reservoir and a source for reinfection of vagina when it is recurrent candidal vulvovaginitis. In the cases of determination of fungi in vagina, they are almost found in feces, and vaginal and intestinal strains are identical at that. Usually candidosis have endogenous character as a wake of dysbiosis, metabolic disturbance and immune system dysfunction.

Considering that *C. albicans* strains isolated from the patients with candidal vulvovaginitis and carrier essentially don't differ, it is possible to draw a conclusion about leading role of immune system in development of candidal vulvovaginitis.

At present the following antimycotic agents for treatment of candidal vulvovaginitis are known. These are imidazoles: clotrimazole, miconazole, oxiconazole, bifonazole, econazole, omoconazole, fenticonazole, isoconazole, terconazole, tioconazole, ketoconazole. Ciclopirox. Allylamines: naftifine. Polyene antibiotics: aniphotericin B, nystatin, levorin and natamycin. Triazoles: fluconazole, itraconazole and other fungicidal and fungistatic preparations.

All these antimycotics are included in the formulation of the pharmaceuticals forms for local and systemic treatment of candidal vaginitis and vulvovaginitis and also in the formulation of creams, emulsions and gels for applying to skin and mucous membrane where mycotic lesion places.

Prebiotics that are indigestible elements of foodstuffs which stimulate growth and development of bacteria dominant species in large intestine microbiocenosis in human body are known. It is lactobacilli and bifidobacteria which use prebiotics as a source of carbohydrates (see U.S. Pat. No. 6,455,068, issued Sep. 24, 2002, incorporated herein by reference in its entirety).

As to chemistry prebiotics are short chain oligo- and disaccharides (fructooligosacharides, galactooligosacharides, maltooligosaccharides, lactulose etc.) that are included into many foodstuffs. In the human body oligosaccharides don't split in the upper gastrointestinal tract and reach a large intestine without changing. Here they are utilized by bifidobacteria and lactobacilli, that is why they are named as "bifidogenic factor".

Stimulation of indogenous intestine microflora growth is connected to inhibition of pathogenic microflora growth, barrier function increase of intestinal mucous membrane and resistance to colonization of the intestine by an extraneous microflora including fungi and yeast.

Normal vaginal microflora contents gram-positive and gram-negative aerobic and anaerobic microorganisms.

Lactobacilli are vaginal microflora dominant.

Optimal conditions of their cultivation are anaerobic conditions when pH value is low (5.5-6.5).

Vaginal microflora of healthy woman completely protects vagina against superinfection by pathogenic bacteria and fungi, supporting low pH value.

By results of microbiological examination of healthy women in reproductive age lactobacilli are determined in vaginal microflora in 97.8% of cases (among them *Lactobacillus acidophilus* in 86.7%), bifidobacteria in 62.2% (among them *Bifidobacterium adolescentis* in 20.0%). According to various data lactobacilli present in vaginal contents in 70-100% of cases.

Decrease of vaginal lactobacilli titer is a result of reducing competition for nutrient substrates due to increase of pH values under circumstances of intense growth and reproduction of opportunistic microflora, which under normal conditions is suppressed by lactic acid producers.

Protective properties of the normal vagina microflora against exogenous pathogens are fulfilled in different ways: by antagonistic activity, competition for substrates, ability to produce lysozyme, adhesive properties, but undoubtedly its main mechanisms are lactic acid and hydrogen peroxide producing.

Thus, the main therapeutic challenge in candidal vulvovaginitis treatment is a restoration of normal vaginal microflora, when physiological mechanisms of the colonization of mucous membrane by saprophytes promote growth suppression of potential pathogens which are *Candida* as usual.

Antimycotics inhibit the growth of fungi and promote the elimination of causative agent, but don't create conditions for restoring normal vaginal microflora that provokes recurrent vaginal candidosis by permanent physiological *Candida* superinfection. Use of prebiotic lactulose in the form of vaginal tampons (see U.S. Pat. No. 3,860,707, issued Jan. 14, 1975, incorporated herein by reference in its entirety) was suggested to restore normal microflora in the treatment of candidal vulvovaginitis.

However a disadvantage of the invention is a usage of lactulose in the form of syrup which has more than 40% of impurities of other saccharides (lactose, fructose, and galactose) which stimulate growth of opportunistic and pathogenic microorganisms.

Suggested tampon form impregnated with a liquid lactulose syrup is inconvenient in use because during application part of lactulose is squeezed from a tissue and spoils the underclothes. Besides usage of tampon impregnated with lactulose syrup, is dangerous, because it can cause mass reproduction and lysis of pathogenic microorganisms inside a tampon and absorption of bacterial endo- and ectotoxins by vaginal mucous membrane.

Tampons impregnated with lactulose syrup does not contain antiseptic components, therefore *Candida* elimination occurs slowly during normal vaginal flora restoration and competitive inhibition of fungi growth, considering a competition for nutritious substrates in the microbial association presented by bacilli, bacteria and fungi.

BRIEF DESCRIPTION OF THE DRAWINGS

The present invention is further illustrated by the attached FIGS. 1-7.

Figure 1:
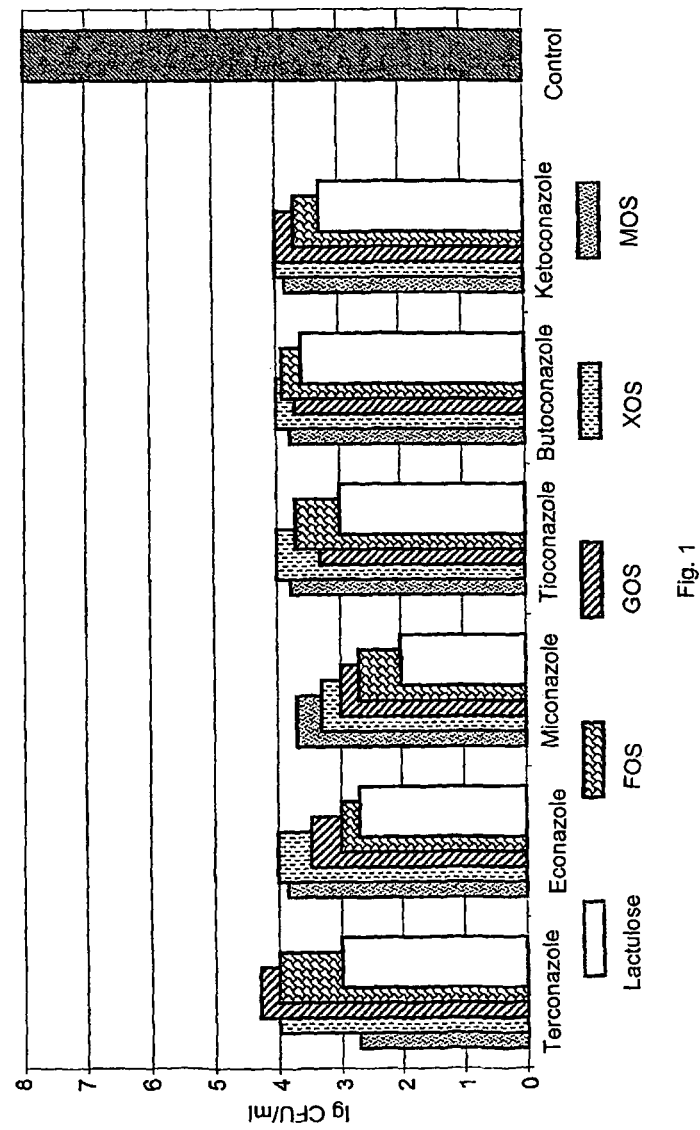
FIG. 1 and FIG. 2 present the diagrams of the therapeutic efficacy of azoles: terconazole, tioconazole, butoconazole, ketoconazole, clotrimazole, miconazole, omoconazole, fenticonazole, oxiconazole, bifonazole, econazole, isoconazole (hereunder showed below the horizontal axis) with prebiotics (hereunder designated by different hatching of diagram columns) on the 7th day of treatment of experimental vaginitis in rats.

Abbreviations used in FIGS. 1-5: FOS—fructooligosaccharides (Raftiline HP, Orafti, Belgium), GOS—galactooligosaccharides (Oligomate 55, Yakut, Japan), XOS—Xilooligosaccharides (Xylooligo-95P, Suntory), MOS—maltooligosaccharides (Maltotetraose, Chemos GmbH, Germany), IMO—isomaltooligosaccharides (IMO, Chemos GmbH, Germany), Lactulose—(Sigma-Aldrich, USA).

Values of the relevant microflora Ig concentration by CFU/ml are plotted on the vertical axis in the FIGS. 1-7.

BRIEF DESCRIPTION OF THE INVENTION

Technical task of the invention is creation of an effective pharmaceutical composition and a way of candidosis vulvovaginitis treatment. The technical result to provide a decision of the problem is that fixed antimycotic and prebiotic pharmaceutical composition for local application is offered, for example, in the pharmaceutical dosage form of vaginal suppository. At candidosis vulvovaginitis treatment the composition formulation allows to achieve synergistic therapeutic effect: stimulation of normal vaginal microflora growth by prebiotics and inhibition of growth and elimination of pathogenic Sapdida fungi by modern antimycotics.

The essence of the invention consists in performance of the pharmaceutical antimycotic and prebiotic composition for prevention and treatment of vaginosis, vaginitis and a vulvovaginitis in the form suitable for local application.

For different realization of antimycotic and prebiotic pharmaceutical composition antibiotics and fungicidal drug products selected from the group of azoles are used as antimycotics: terconazole, tioconazole, butoconazole, ketoconazole, clotrimazole, miconazole, omoconazole, fenticonazole, oxiconazole, bifonazole, econazole, isoconazole; So are drug products selected from the group of allylamines: naftifine, terbinafine; polyene antibiotics: amphotericin B, natamycin, nystatin, levorin; nitrofurans: nifuratel, furazolidone, and their pharmaceutically acceptable combinations are used. Preferably the pharmaceutical composition contains not less than one antimycotic at concentration range from 0.0001% to 5% (weight/volume) per composition mass.

For different realization of the pharmaceutical composition it contains pharmaceutically acceptable concentrations of prebiotics selected from the groups of natural or synthetic saccharides and oligosaccharides: lactulose, fruitooligosaccharides, galactooligosaccharides, xylooligosaccharides, maltooligosaccharides, isomalto-oligosaccharides with polymerization degree from 2 to 30, and its combinations.

Preferably the pharmaceutical composition contains prebiotics at concentration range from 0.1% to 40.0% (weight/volume) per composition mass.

For different realization of antimycotic and prebiotic pharmaceutical composition for prevention and treatment of vaginosis, vaginitis, and vulvovaginitis is produced in the following pharmaceuticals dosage forms: suppositories, pessaries, globules, soft capsules, tampons, creams, gels, emulsions and other forms for local application. The essence of the invention as a method of treatment of vaginosis, vaginitis, and vulvovaginitis with fungal or bacterial etiology consists in usage of antimycotic and prebiotic pharmaceutical composition in dosage form for local application, based on inhibition of pathogenic fungi and yeast growth by antimycotics with simultaneous stimulation of normal vaginal microflora growth.

Preferably at the method of vaginosis, vaginitis, and vulvovaginitis treatment with fungal or bacterial etiology applying antimycotic and prebiotic pharmaceutical composition this composition is used for local therapy in the following dosage form: suppositories, globules, pessaries, tampons, soft gelatin capsules, pills, creams, ointments, gels, suspensions, solutions etc.

In these cases usage of antimycotics failed to suppress growth and reproduction of lactobacilli and bifidobacteria which are dominant species in vaginal microbiocenosis is provided.

Provision process of the announced pharmaceutical composition in suppository dosage form provides preparing of a target amount of antimycotics and prebiotics, mixing of the components, adding components to the molten suppository base suitable for making vaginal suppositories, molding suppositories and packaging in blisters. Suppository formulations can contain additional components to improve pharmaceutical and consumer suppositories' properties (emulsifiers, flavorings etc.)

Examples

1. Adjustment of Suppository Experimental Composition

Vaginal suppositories with antimycotic composition of natamycin and nifuratel are combined with lactulose prebiotics using different suppository bases and the following component ratio are presented as examples.

| Suppository Composition No1 | |
| --- | --- |
| Components | Weight, mg |
| Natamycin | 100 |
| Lactulose | 200 |
| Cremophor RH40* | 200 |
| Witepsol | 1500 |
| TOTAL | 2000 |

| Suppository Composition No2 | |
| --- | --- |
| Components | Weight, mg |
| Natamycin | 100 |
| Lactulose | 200 |
| Cremophor RH40* | 200 |
| PEG | 1500 |
| TOTAL | 2000 |

| Suppository Composition No3 | |
| --- | --- |
| Components | Weight, mg |
| Nifuratel | 100 |
| Lactulose | 200 |
| Cremophor RH40* | 200 |
| Witepsol | 1500 |
| TOTAL | 2000 |

| Suppository Composition No4 | |
| --- | --- |
| Components | Weight, mg |
| Nifuratel | 100 |
| Lactulose | 200 |
| Cremophor RH40* | 200 |
| PEG | 1500 |
| TOTAL | 2000 |

*Kremofor RH40 (polioxyl)-hydrogenated castor oil.
(Polioxyl-40 Hydrogenated Castor Oil) according to European Pharmacopoiea (EP) and (USP/NF).
Suppositories No1 and No3 were prepared on suppository base of Witepsol (Witepsol H15, W35), suppositories No2 and No4 on the base of Polyethylene glycol (PEG 1500).

2. Experimental Model Study of Therapeutic Efficacy

Earlier described rat infection model (De Bernardis F., et al, 1999) was used in the experiment to model candidal vaginosis infection and to study candidosis treatment. Spayed female Wistar rats (80-100 g) took estradiol benzoate 0.5 mg in the form of hypodermic injection daily for 5 days. On the sixth day rats were intravaginally infected with 0.1 ml of $C.$ $albicans$ ATCC 10231 cell suspension, containing 10.7 yeast cells. Cell suspension was intravaginally administered into laboratory animals using syringe with special cannula. Before injection strain $C.$ $albicans$ ATCC 10231 was cultivated in shake-flask propagator (200 rpm) at temperature 300 C in liquid nutrient medium containing 1% of yeast extract, 2% of peptone and 2% of glucose. After 48 hours incubation cells were collected by centrifugation, washed, resuspended in 0.9% NaCl solution, and then cells were used for vaginal infection in rats.

After the infection of animals with $C.$ $albicans$ 10231 strain bacteriological tests of vaginal fluid of rats were made every 2 days by inoculation 1 μl of vaginal secret on Sabouraud agar plates, containing 50 mkg/ml of chloramphenicol. Then agar plates were cultivated within 48 hours at 350 C with calculation of pigmented colonies of $C.$ $albicans$. Development of experimental candidal vaginitis in rats was bacteriologically monitored by change of yeast cell titers in the control and experimental groups' vaginal fluid. Thus, on the model of spayed rats experimental animals population with candidal infection of mucous membrane of vagina was obtained. In the sequel the animals were used for estimation of therapeutic activity of the suggested antimycotic and prebiotic compositions. For estimation of therapeutic efficacy of each composition 5 rats with bacteriologically confirmed vagina candidal infection were used, the control animal group (10 rats) was kept without treatment. Local therapy of experimental candidal vaginitis of rats with bacteriologically confirmed vagina infection was made by different compositions in the form of a vaginal suppository. Special globules simulating vaginal suppository, containing doses of active components 50 times less than it is recommended for formulation of the formal human vaginal suppository with antimycotics were prepared for rats. Formulation of the suppository mass of compositions wasn't changed.

Table 1 presents formulations of antimycotics and prebiotics compositions that were used for producing suppository and globules for rats.

TABLE 1

Antimycotics and prebiotics compositions for treatment experimental candidal vaginitis in rats

| Antimycotics, Mg | Prebiotic concentration (mg)* | | | | | |
|---|---|---|---|---|---|---|
| | FOS 25 | GOS 30 | XOS 30 | MOS 20 | IMO 20 | Lactulose 20 |
| Azoles**: | | | | | | |
| econazole | 1.0 | 1.0 | 1.0 | 1.0 | 1.0 | 1.0 |
| terconazole | 1.6 | 1.6 | 1.6 | 1.6 | 1.6 | 1.6 |
| miconazole | 2.0 | 2.0 | 2.0 | 2.0 | 2.0 | 2.0 |
| Allylamines: | | | | | | |
| terbinafine | 5.0 | 5.0 | 5.0 | 5.0 | 5.0 | 5.0 |
| naftifine | 4.0 | 4.0 | 4.0 | 4.0 | 4.0 | 4.0 |
| Polyene antibiotics: | | | | | | |
| natamycin | 2.0 | 2.0 | 2.0 | 2.0 | 2.0 | 2.0 |
| nystatin | 5.0 | 5.0 | 5.0 | 5.0 | 5.0 | 5.0 |
| levorin | 5.0 | 5.0 | 5.0 | 5.0 | 5.0 | 5.0 |
| nitrofurans: | | | | | | |
| nifuratel | 5.0 | 5.0 | 5.0 | 5.0 | 5.0 | 5.0 |
| furazolidone | 4.0 | 4.0 | 4.0 | 4.0 | 4.0 | 4.0 |

*FOS—fructooligosaccharides (Raftiline HP, Orafti, Belgium), GOS—galactooligosaccharides (Oligomate 55, Yakut, Japan), XOS—Xilooligosaccharides (Xylooligo-95P, Suntory), MOS—maltooligosaccharides (Maltotetraose, Chemos GmbH, Germany), IMO—isomaltooligosaccharides (IMO, Chemos GmbH, Germany), Lactulose - (Sigma-Aldrich, USA).
**All others azoles in formulation of compositions had similar concentration ranged from 1.0 to 2.0 mg.

Figure 2:
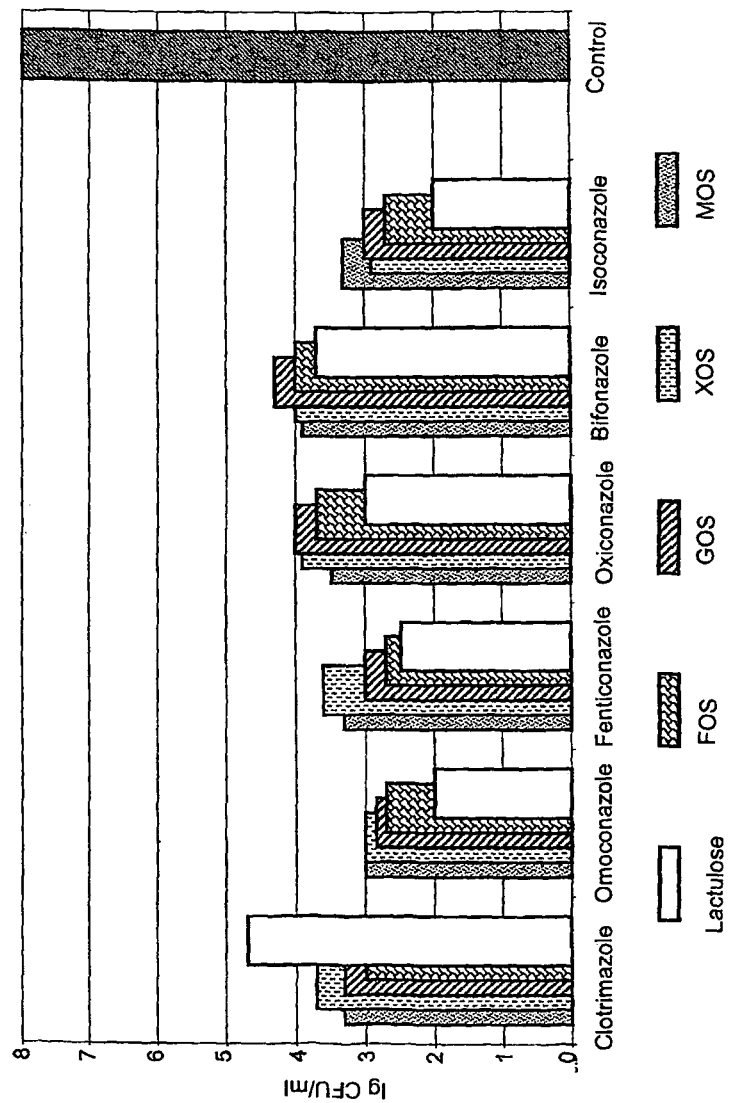
Figure 3:
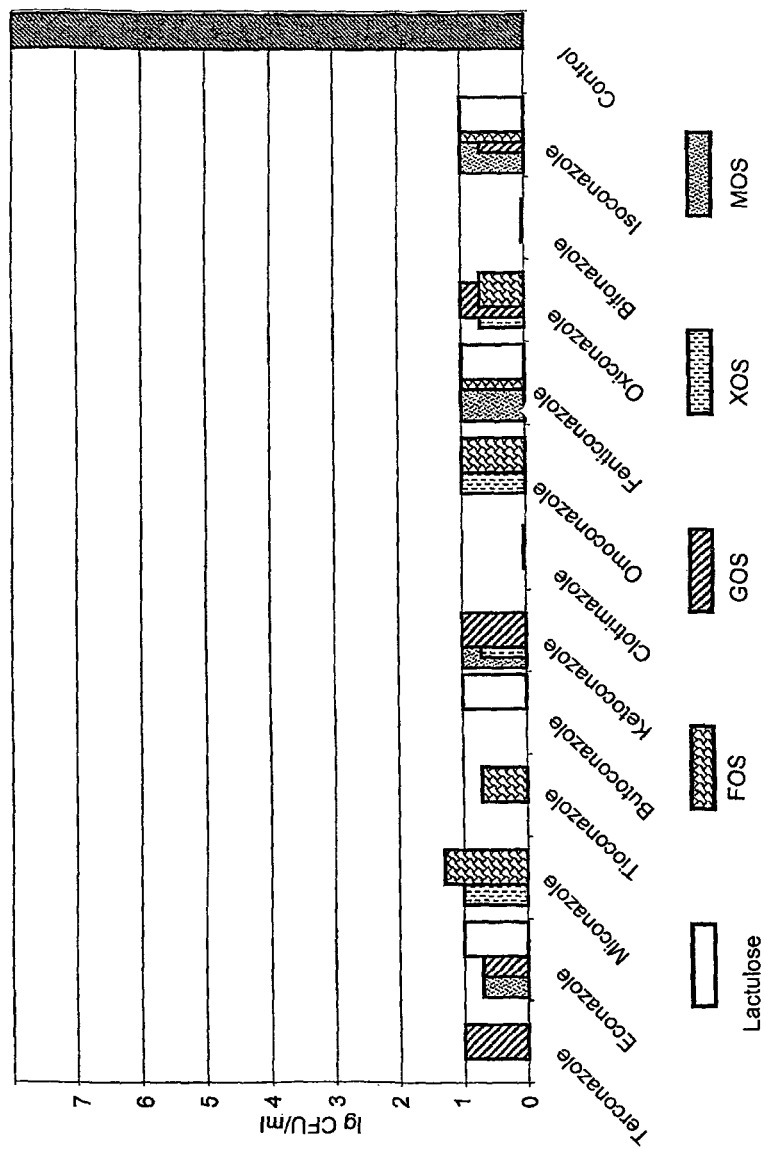
FIG. 3 presents the diagrams of the therapeutic efficacy of azoles: terconazole, tioconazole, butoconazole, ketoconazole, clotrimazole, miconazole, omoconazole, fenticonazole, oxiconazole, bifonazole, econazole, isoconazole (hereunder they are showed below the horizontal axis) with prebiotics on the 14th day of treatment of experimental vaginitis in rats.
Figure 4:
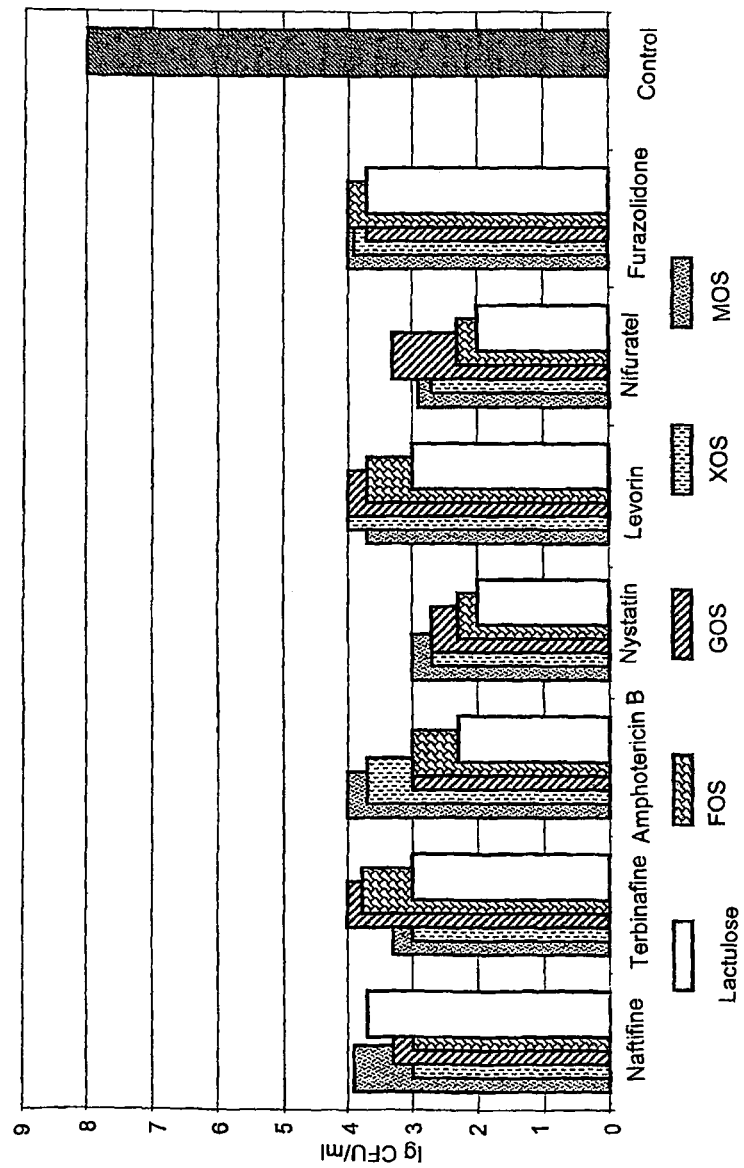
FIG. 4 presents the diagrams of the therapeutic efficacy of compositions of allylamines, polyenes nitrofuranov with prebiotics on the 7th day of treatment of experimental vaginitis in rats.
Figure 5:
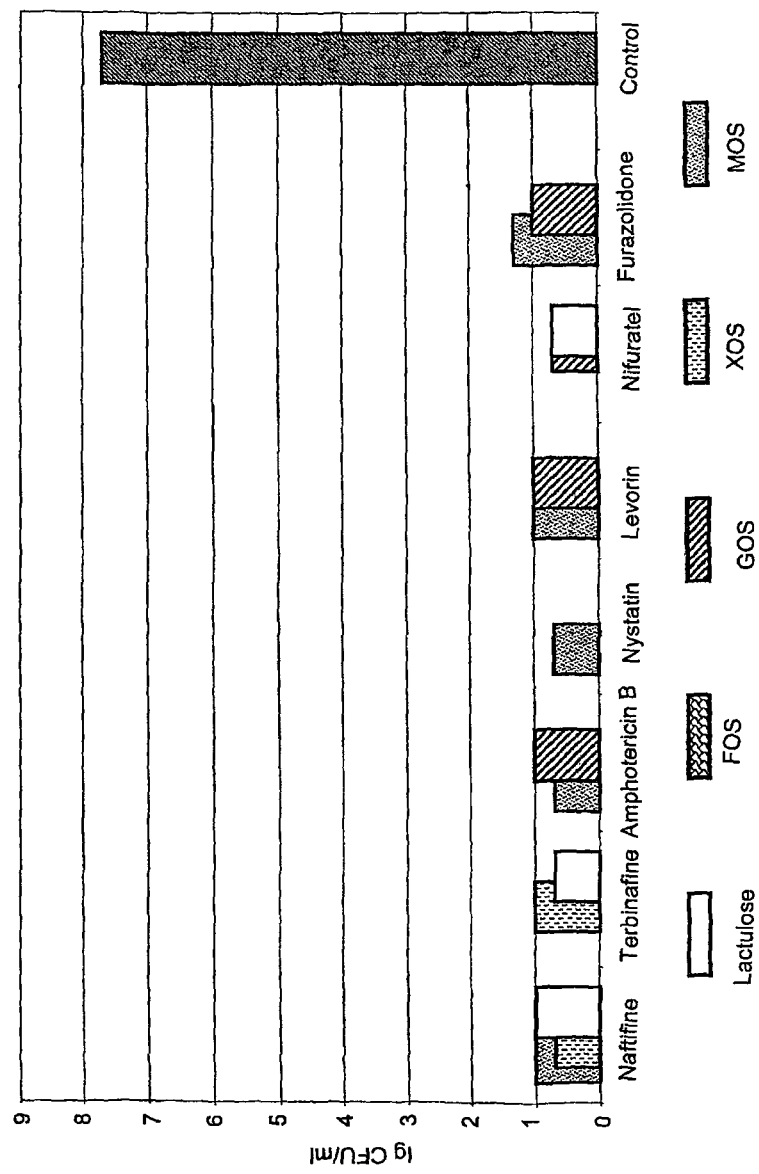
FIG. 5 presents the diagrams of the therapeutic efficacy of compositions of allylamines, polyenes nitrofurans with prebiotics on the 14th day of treatment of experimental vaginitis in rats.

Globules with antimycotics were introduced into the vagina of experimental rats daily from 6th to 12th day of the experiment. Treatment efficacy was estimated by results of bacteriological research of rats' vaginal fluid on presence of *C. Albicans* fungi. 10 rats without treatment which were bacteriologically surveyed each 48 hours on presence of *Candida* in vaginal fluid were a control in each group. The results of antimycotic action of compositions at vaginal introduction into rats are presented on diagrams (FIGS. 1-5). Submitted data indicates that at local therapy all examined compositions included in experimental suppositories actively suppressed development of candidal vaginal infections in rats. In two days of treatment *Candida* titer in vaginal fluid decreased 10.4-10.5 times while *Candida* titer of control animals at bacteriological survey remained without changes (FIGS. 1, 2, 4). In next 7 days of treatment survey on the 14th day of experiment indicated that infection was almost arrested and it was possible to allocate only separate *C. albicans* colonies in vaginal discharge in rats (FIGS. 3, 5). More than 60% of the experimental animals received treatment almost fail to reveal *Candida* by bacteriological methods during the survey on the 14th day.

Thus, in the conditions of experimental candidal infection in rats, caused by *C. albicans* ATCC 10231 strains, specific fungicidal activity of fungi infection local therapy by antimycotic and prebiotic pharmaceutical compositions is shown.

3. Clinical Study of Compositions

Clinical study were spent to improve therapeutic efficacy and safety of with lactulose pharmaceutical composition in the dosage form of suppository and to obtain the direct clinical data confirming synergistic effect of natamycin antimycotic with prebiotic in the patients with candidal vaginitis or vulvovaginitis.

30 patients were included in the study aged from 20 to 45 with candidal vaginitis or vulvovaginitis first time revealed.

Candidosis was diagnosed on the base of objective clinical data (survey of vaginal mucous membrane by gynecological specula), patient complaints about vaginal discharge, burning, irritation of vaginal mucous membrane. Some patients complained of dysuria and dispareunia.

The diagnosis was confirmed bacteriologically by method of direct microscopy of vaginal smear and isolation of *Candida* in a pure culture.

Vaginal fluid was analyzed on presence of chlamydia, mycoplasma and ureaplasma using polymerase chain reaction (PCR).

All 30 patients included in the clinical study took part in microbiological diagnostics of vaginal fluid for detection titer of *bifidobacterium* and *lactobacillus* in vaginal microflora composition before the beginning and after the termination of the course of experimental suppository treatment.

The material was analyzed in Laboratory of Microbiology of the D. O. Ott Research Institute of Obstetrics and Gynecology, Saint Petersburg. Vaginal discharge was tested by direct inoculation of solid and liquid mediums: blood agar, MRS medium, broth and Sabouraud agar. The samples were cultivated in aerobic and microaerophilic conditions (2-5% of oxygen) at temperature of 37 degrees.

Strains were identified on the base of analysis of colony and cell morphology, cultural, biochemical and tinctorial properties of microorganisms.

Released lactobacillus isolates were also identified by catalase and oxidase activity.

The bacterium quantity in the material were estimated by calculation of colonies on dense nutrient mediums which were represented in the form of Ig CFU/ml.

All patients with formulated diagnosis candidal vaginitis included in research were randomized in three groups by 10 persons:

the first group took local treatment by vaginal suppositories with natamycin and lactulose 1 time per day for 6 days (composition No 1);

the second group also took local treatment by vaginal suppositories with natamycin and lactulose 1 time per day for 6 days (composition No 2); and the control group took local treatment by vaginal suppositories "пимафуцин" with antimycotic natamycin, manufactured by Yamanouchi Europe b.v. 100 mg 1 time per day for 6 days.

The result of the clinical study confirmed that pharmaceutical composition of natamycin with lactulose possesses high therapeutic efficacy in relation to causative agent of candidal vaginitis (see Table 2, 3) and restores normal vaginal microflora (see FIG. 7) that is a crucial criterion for candidosis therapy.

Figure 6:
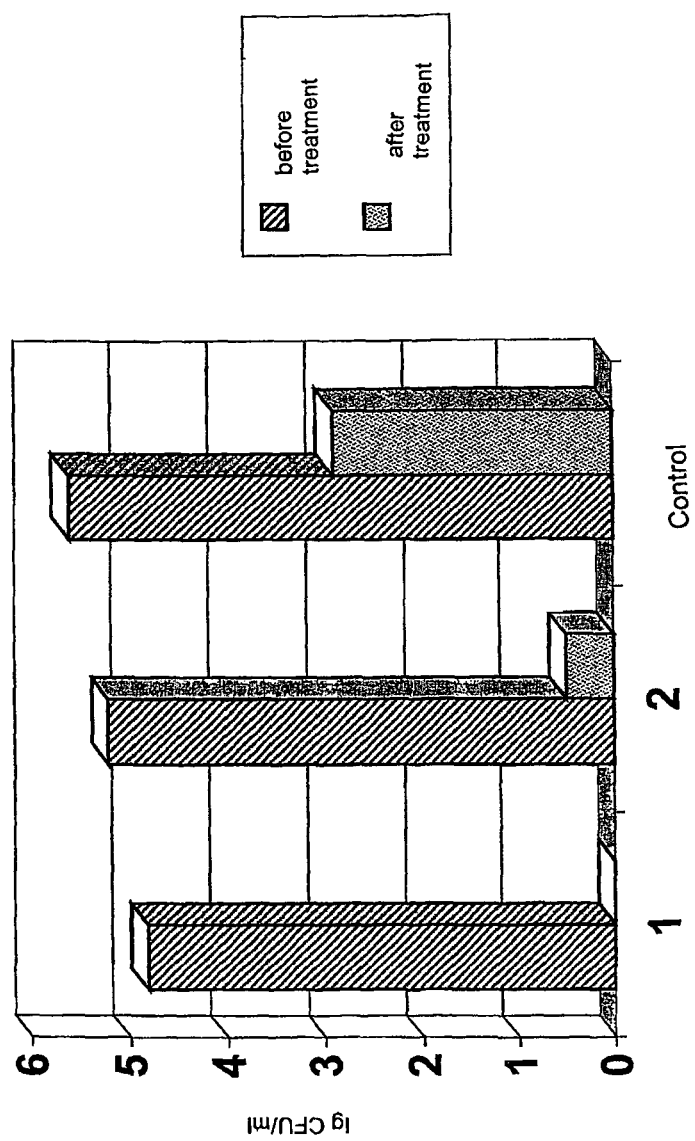
FIG. 6 presents the diagrams of *Candida* spp. concentration before and after treatment (hereunder designated by different hatching) at the patients with candidal vulvovaginitis in the 3 groups (one group is control).
Figure 7:
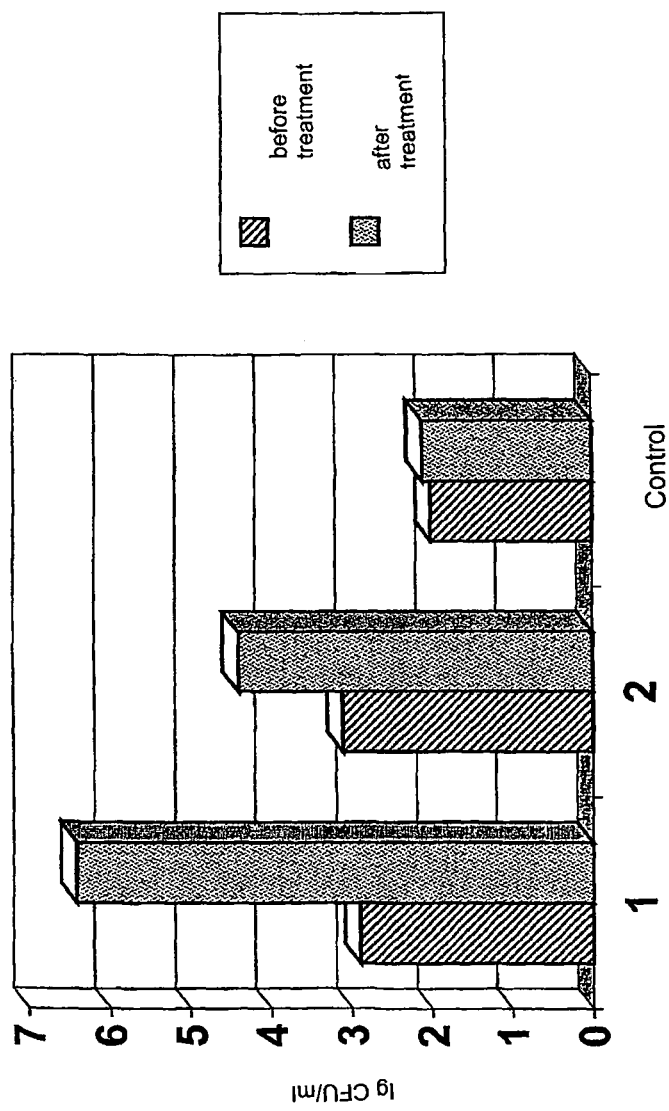
FIG. 7 presents the diagrams of vaginal lactobacilli concentration before and after treatment at the patients with candidal vulvovaginitis in the 3 groups (one group is control).

The analysis of vaginal microflora species composition of the first group patients after treatment course by experimental suppositories with natamycin and lactulose revealed that elimination of *Candida* fungi occurred in 100% of cases (see Table 2; FIG. 6), simultaneously intensity of clinical symptoms of candidosis decreased. Bacteriological research showed that lactobacillus titer in vaginal fluid increased 1000 times and more (see FIG. 7). In the second group succeeding elimination of causative agent is registered in 90% of cases (see FIG. 2), at the same time in the control group recovery from Candida after the therapy course observed only for 50% of patients (see Table 4; FIG. 6).

Inclusion of lactulose in complex antimycotic therapy allows keeping and essentially increasing the number of lactobacilli in vaginal fluid that, undoubtedly, raises local immunity and interferes with development of fungi infection. It is a synergism of natamycin and lactulose action in adequate suppository base is seems to improve clinical efficacy of the local candidosis therapy. Thus, the clinical data objectively confirms efficacy of suggested way to treat for vaginal candidosis, proceeding from the conception of synergistic action of antimycotics and prebiotics as a part of the fixed composition and microbiocenosis normalization at the expense of increase of vaginal mucous membrane colonization by lactobacilli.

The formulation No 1 prepared on Witepsol suppository base is proved to be the most clinically succeeding. The formulation No 2 prepared on PEG 1500 base was a little less effective, however in this case results also significantly exceeded the indicators that were registered in the control group (see Table 2-4).

Suggested pharmaceutical composition becomes new prospective means and method of treatment vaginal mucous membrane candidosis involvement due to clinical efficacy, absence of side effects, low frequency of relapses and patient compliance of local therapy by experimental suppositories.

TABLE 2

Results of laboratory study in the first group.

| Indicators | BK, n = 10 | |
| --- | --- | --- |
| | Before therapy | After therapy |
| Isolation of Candida from vaginal fluid | 100% | 0% |
| Presence of Leukocytes in endocervical smear (from ½ to whole field of microscope) | 60% | 0% |
| Presence of Leukocytes in vaginal mucous membrane from 20 to 40 in field of microscope | 60% | 10% |

TABLE 3

Results of laboratory researches in the second group.

| Indicators | BK, n = 10 | |
| --- | --- | --- |
| | Before therapy | After therapy |
| Isolation of Candida from vaginal fluid | 100% | 10% |
| Presence of Leukocytes in endocervical smear (from ½ to whole field of microscope) | 60% | 30% |
| Presence of Leukocytes in vaginal mucous membrane from 20 to 40 in field of microscope | 70% | 30% |

TABLE 4

Results of laboratory study in the control group.

| Indicators | BK, n = 10 | |
| --- | --- | --- |
| | Before therapy | After therapy |
| Isolation of Candida from vaginal fluid | 100% | 50% |
| Presence of Leukocytes in endocervical smear (from ½ to whole field of microscope) | 60% | 40% |
| Presence of Leukocytes in vaginal mucous membrane from 20 to 40 in field of microscope | 70% | 70% |

INDUSTRIAL APPLICABILITY

The invention is realized by means of versatile facilities that are widespread in industry.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are incorporated herein by reference, further discussion is deemed unnecessary.

What is claimed is:

1. A pharmaceutical composition, comprising: an antimycotic component and a prebiotic component, wherein the pharmaceutical composition is effective for prevention and treatment of vaginosis, vaginitis and vulvovaginitis in a dosage form suitable for local application; wherein the antimycotic component comprises one or more compound selected from the group consisting of terconazole, tioconazole, butoconazole, ketoconazole, clotrimazole, miconazole, omoconazole, fenticonazole, oxiconazole, bifonazole, econazole, isoconazole, naftifine, terbinafine, amphotericin B, natamycin, nystatin, levorin, nifuratel, furazolidone, and their pharmaceutically acceptable combinations; and wherein the prebiotic component is lactulose present in pharmaceutically acceptable concentrations, mixed in the composition such that the composition comprises, in weight/volume concentrations per composition mass:
(i) antimycotic, from 0.0001% to 5%;
(ii) lactulose, from 0.1% to 40%;
(iii) the balance: dosage form base and/or excipients
wherein said composition is both water and lipid soluble;
wherein the pharmaceutical composition further comprises PEG (polyethylene glycol) and/or Witepsol as a base; wherein the pharmaceutical composition further comprises Cremophor RH40 as a solubilizing agent.

2. The pharmaceutical composition for prevention and treatment of vaginosis, vaginitis and vulvovaginitis according to in claim 1, wherein said composition is produced in the form of suppositories, pessaries, globules, soft capsules, tampons, creams, gels, emulsions and other forms suitable for local application.

3. The pharmaceutical composition referred to in claim 1, wherein said base is a suppository base.

4. The pharmaceutical composition for prevention and treatment of vaginosis, vaginitis and vulvovaginitis referred to in claim 1, wherein the antimycotic component is one or more compound selected from the group consisting of terconazole, tioconazole, butoconazole, ketoconazole, clotrimazole, miconazole, omoconazole, fenticonazole, oxiconazole, bifonazole, econazole, isoconazole, naftifine, terbinafine, amphotericin B, levorin, nifuratel, furazolidone, and their pharmaceutically acceptable combinations.

5. A method of treatment of vaginosis, vaginitis and vulvovaginitis of fungal or bacterial etiology, said method comprising: applying a combined antimycotic and prebiotic pharmaceutical composition in a dosage form suitable for local application, wherein said composition causes inhibition of pathogenic fungi and yeast growth by antimycotics with simultaneous stimulation of normal vaginal microflora growth; and wherein said composition comprises as a prebiotic a component selected from the group consisting of fructooligosaccharides, galactooligosaccharides, lactulose, isomalto-oligosaccharides, xylooligosaccharides, maltooligosaccharides, and their pharmaceutically acceptable combinations, such that the composition comprises in weight/volume concentrations per composition mass:

(i) antimycotic, from 0.0001% to 5%;
(ii) prebiotic, from 0.1% to 40%; and
(iii) the balance: dosage form base and/or excipients
wherein said composition is both water and lipid soluble;
wherein the pharmaceutical composition further comprises PEG (polyethylene glycol) and/or Witepsol as a base; wherein the pharmaceutical composition further comprises Cremophor RH40 as a solubilizing agent.

6. The method of treatment of vaginosis, vaginitis and vulvovaginitis of fungal or bacterial etiology referred to in claim 5, wherein the pharmaceutical antimycotic and prebiotic composition is used for local therapy in the form of suppositories, globules, pessaries, tampons, soft gelatin capsules, pills, creams, ointments, gels, suspensions or solutions.

7. A pharmaceutical composition for prevention and treatment of vaginosis, vaginitis and vulvovaginitis, comprising: an antimycotic component and a prebiotic component in a dosage form suitable for local application, wherein the prebiotic component is selected from the group consisting of: fructooligosaccharides, galactooligosaccharides, lactulose, maltooligosaccharides, isomalto-oligosaccharides, xylooligosaccharides, and their pharmaceutically acceptable combinations, and wherein further the prebiotic component is present in the pharmaceutical composition in a ratio to the antimycotic component of from 1:1 to 30:1 by weight
wherein said composition is both water and lipid soluble;
wherein the pharmaceutical composition further comprises PEG (polyethylene glycol) and/or Witepsol as a base; wherein the pharmaceutical composition further comprises Cremophor RH40 as a solubilizing agent.

8. The pharmaceutical composition referred to in claim 7, wherein the antimycotic component is selected from the group consisting of: amphotericin B, bifonazole, clotrimazole, fenticonazole, furazolidone, isoconazole, levorin, naftifine, natamycin, nifuratel, nystatin, omoconazole, oxiconazole, terbinafine, and their pharmaceutically acceptable combinations.

* * * * *